United States Patent [19]

Nawaz

[11] Patent Number: 4,591,483
[45] Date of Patent: May 27, 1986

[54] NOBLE METAL ALLOYS FOR DENTAL USES

[75] Inventor: M. H. A Nawaz, Neulingen, Pakistan

[73] Assignee: Degussa Aktiengesellschaft, Frankfurt, Fed. Rep. of Germany

[21] Appl. No.: 704,462

[22] Filed: Feb. 22, 1985

[30] Foreign Application Priority Data

Feb. 24, 1984 [DE] Fed. Rep. of Germany ....... 3406712

[51] Int. Cl.[4] .......................... C22C 5/02; C22C 5/04; C22C 30/00
[52] U.S. Cl. .................................... 420/463; 420/464; 420/508; 420/512; 420/580; 420/581; 420/582; 420/587; 420/589; 433/207
[58] Field of Search ............... 420/463, 464, 508, 512, 420/580, 581, 582, 587, 589; 433/207

[56] References Cited

U.S. PATENT DOCUMENTS

| | | | |
|---|---|---|---|
| 4,123,262 | 10/1978 | Cascone | 420/508 |
| 4,179,286 | 12/1979 | Knosp | 420/463 |
| 4,201,577 | 5/1980 | Ingersoll et al. | 420/589 |
| 4,205,982 | 6/1980 | German | 420/508 |
| 4,400,350 | 8/1983 | Wagner | 420/464 |
| 4,419,325 | 12/1983 | Prasad | 420/464 |
| 4,451,639 | 5/1984 | Prasad | 420/508 |

FOREIGN PATENT DOCUMENTS

| | | | |
|---|---|---|---|
| 1533233 | 10/1970 | Fed. Rep. of Germany . | |
| 2440425 | 3/1976 | Fed. Rep. of Germany . | |
| 2944755 | 5/1980 | Fed. Rep. of Germany . | |
| 0107436 | 6/1983 | Japan | 420/463 |
| 2048939 | 12/1980 | United Kingdom | 420/463 |

*Primary Examiner*—L. Dewayne Rutledge
*Assistant Examiner*—Robert L. McDowell
*Attorney, Agent, or Firm*—Cushman, Darby & Cushman

[57] ABSTRACT

There are described noble metal alloys for dental purposes, especially for firing on dental porcelain which are low melting, do not discolor the porcelain, are repeatedly castable, and making possible brazing joints. These alloys containing 20 to 65% gold, 25 to 65% palladium, 0 to 7% gallium, 0.2 to 11% indium and/or tin, 0 to 2% copper, 0.05 to 1% ruthenium, iridium and/or rhenium, 0 to 1% vanadium, 0 to 1% iron and additionally 0.5 to 15% cobalt, with the proviso that the content of base metals must exceed 5%.

5 Claims, No Drawings

NOBLE METAL ALLOYS FOR DENTAL USES

BACKGROUND OF THE INVENTION

The invention is directed to metal alloys for use in dentistry, especially for use with dental porcelains in making dental restorations.

The customary dental alloys having a gold content between 70 and 80 weight percent are well suited for the production of dental prostheses (e.g., German OS No. 1533233). They are resistant to corrosion in the oral cavity and can be worked with easily.

In recent times because of the high price of gold, alloys have been employed in which part of the gold content is replaced by palladium. In order to match the good melting casting properties of the high gold content alloys, the silver content has been increased in several of these reduced gold alloys (e.g., German Pat. No. 2440425). However, an aesthetic disadvantage of such alloys is that the dental porcelain can be discolored by the silver during the firing process.

The exact mechanism which causes such discoloration is not known. However, alloys without silver do not show this behavior.

The known silver free gold-palladium alloys (e.g., German Pat. No. 2813813 and related Knosp U.S. Pat. No. 4,179,286) in contrast have a high liquidus temperature, which makes melting difficult in the customary dental casting machines. Besides, such alloys do not show the mold-filling capacity and the flow properties of the high gold containing or the reduced gold, but silver containing alloys, which can lead to defects in the castings and to problems such as bubbles in the fired on porcelain. Alloys suited for firing on of dental porcelains must additionally posses a thermal expansion coefficient higher than that of the porcelain, in order to avoid tensile stresses in the porcelain layer which can lead to cracks in the porcelain. However, the expansion coefficient of the reduced gold, silver free alloys is found to be too low. This as well frequently leads to cracks or fissures in the porcelain.

In order to improve the industrial efficiency, it is necessary to reuse the casting waste. Therefore, the alloys must be melted several times and be able to cast without significantly changing their properties which can lead to hot tears in the castings or to spalling of the porcelain.

From Prasad U.S. Pat. No. 4,419,325, there are known palladium alloys for dental purpose which contain in addition to 35 to 85% palladium, 5 to 15% gallium, 0.1 to 0.5% ruthenium or rhenium, 0 to 50% gold, 0 to 12% copper, 0 to 5% aluminum, and 0 to 13% cobalt. These alloys have a relatively high melting range and do not show optimum bonding to the generally available porcelains. Besides they must be melted under vacuum or inert gas.

In German OS No. 2944755 there are described numerous dental porcelain alloys having about 32 to 63% gold and 29 to 58% palladium which in addition contain 0.5 to 10.55% indium and to which there can be added up to several percent of gallium, tin, cooper, nickel, aluminum, titanium, and silver. However, these alloys degrade with multiple remeltings and then no longer result in dense castings.

After firing the porcelain it is customary to braze together the different pieces of a dental bridge in a furnace. For this purpose, a flux is used which does not attack the ceramic. It is not possible with the alloys according to German OS No. 2944775 to get ductilely reliable joints with cadmium free brazes. The joint fractures without plastic deformation along the surface between the filler metal and the parent metal.

Hence it was the purpose of the present invention to provide noble metal alloys for dental purposes with reduced gold content compared to conventional gold alloys, especially for firing on of dental porcelains, which are low melting, have a high solidus temperature in order that they do not deform during the firing on of porcelain, do not lead to discolorations in the ceramic, make strong joints with cadmium free dental blazes. Besides, they should be repeatedly meltable and castable in air without degrading in any way.

SUMMARY OF THE INVENTION

The objectives of this invention have been achieved in alloys containing 20 to 65% gold, 25 to 65% palladium, 0 to 7% gallium, 0.2 to 11% indium and/or tin, 0 to 2% copper, 0.05 to 1% of one or more of the elements ruthenium, indium and rhenium, 0.5 to 15% cobalt, 0 to 1% vanadium and 0 to 1% iron.

Especially suited alloys contain 50 to 65% gold, 30 to 40% palladium, 4 to 10% indium, 0 to 2% tin, 1 to 2% gallium, 0.05 to 1% ruthenium, iridium and/or rhenium and 1 to 5% cobalt.

Preferably, alloys with 60 to 65% gold, contain 30 to 35% palladium, 4 to 6% indium, 0 to 2% tin, 1 to 2% gallium, 0.05 to 0.3% ruthenium, iridium and/or rhenium and 1 to 3% cobalt.

The alloys of the invention do not discolor the commercial ceramics in any manner. The alloys are especially low melting and can be melted without problem in commerical casting apparatus, for example resistance heated furnaces or with a propane-oxygen torch. Their flow and mold filling properties result in dense and cavity free castings, even after repeated remeltings. Their solidus temperature is sufficiently high so that the possibility of deformation during the firing process is excluded. Besides, brazed joints with these alloys show high strength and toughness.

After repeated meltings and castings of these alloys, neither hot tears nor cracks in the porcelain were found. The thermal coefficient of expansion is very compatible with that of customary dental ceramics so that even after several months neither fissures nor cracks are ascertainable in the ceramic. The bonding is also very good; it surpasses most of the known fired on alloys.

Because of their good casting behavior, the alloys are also suited as casting alloys for removeable dental prosthesis and as the framework for plastic dentures.

Low gold alloys also exhibit good properties, there are proven good alloys with 50 to 55% gold, 35 to 40% palladium, 6 to 10% indium, 0 to 1% tin, 1 to 2% gallium, 0.05 to 1% ruthenium, iridium and/or rhenium, 1.5 to 12.5% cobalt, 0 to 1% vanadium, and 0 to 1% iron or alloys having 20 to 50% gold, 40 to 60% palladium, 0.2 to 8% indium, 0.2 to 6% tin, 0 to 2% copper, 1 to 5% gallium, 0.05 to 1% ruthenium, iridium and/or rhenium and 2 to 12% cobalt.

The alloys consist of or consist essentially of the stated materials.

Unless otherwise indicated, all parts and percentages are by weight.

DETAILED DESCRIPTION

The following table shows the properties of several of the alloys of the invention.

| COMPOSITION IN % | | | | | | | | | | | Melting Interval | Hardness HV 5 | | |
|---|---|---|---|---|---|---|---|---|---|---|---|---|---|---|
| Au | Pd | In | Sn | Co | V | Fe | Ga | Cu | Ru | Re | Ir | °C. | g | w | a |
| 61.5 | 30.0 | 5.0 | 0.5 | 1.5 | | | 1.2 | | | | 0.2 | 1255–1165 | 230 | 190 | 230 |
| 61.6 | 30.0 | 4.0 | | 2.7 | | | 1.5 | | | | 0.2 | 1245–1145 | 220 | 190 | 245 |
| 55.0 | 35.0 | 6.5 | 0.2 | 2.1 | | | 1.0 | | | | 0.2 | 1275–1150 | 232 | 180 | 232 |
| 55.0 | 35.0 | 6.5 | | 2.1 | | | 1.2 | | | | 0.2 | 1270–1150 | 232 | 201 | 234 |
| 53.5 | 36.0 | 5.6 | | 3.2 | | | 1.5 | | 0.2 | | | 1265–1195 | 230 | 215 | 320 |
| 52.5 | 35.1 | 8.0 | | 2.7 | | | 1.5 | | 0.2 | | | 1220–1145 | 305 | 270 | 305 |
| 52.5 | 35.1 | 8.0 | | 2.2 | 0.5 | | 1.5 | | 0.2 | | | 1220–1145 | 277 | 244 | 283 |
| 52.5 | 33.1 | | 2.0 | 12.2 | | | | 0.2 | | | | 1230–1150 | 217 | 177 | 247 |
| 52.5 | 33.1 | | 2.0 | 11.7 | | | 0.5 | 0.2 | | | | 1220–1140 | 265 | 232 | 321 |
| 52.5 | 35.1 | 8.0 | 0.5 | 2.2 | | | 1.5 | 0.2 | | | | 1220–1150 | 293 | 249 | 293 |
| 52.5 | 35.1 | 7.2 | 1.3 | 2.2 | | | 1.5 | 0.2 | | | | 1220–1150 | 286 | 280 | 303 |
| 52.5 | 35.1 | 8.0 | 0.5 | 2.2 | | | 1.5 | | 0.2 | | | 1220–1145 | 285 | 255 | 305 |
| 51.9 | 37.0 | 6.5 | 0.5 | 2.7 | | | 1.2 | | 0.2 | | | 1260–1190 | 245 | 220 | 245 |
| 51.1 | 37.0 | 7.0 | 0.5 | 2.2 | | 0.5 | 1.5 | | 0.2 | | | 1230–1150 | 255 | 255 | 270 |
| 51.1 | 37.0 | 7.0 | 0.5 | 2.2 | 0.5 | | 1.5 | | 0.2 | | | 1220–1150 | 230 | 215 | 230 |
| 51.1 | 36.5 | 8.0 | | 2.7 | | | 1.5 | | | | 0.2 | 1245–1145 | 260 | 245 | 270 |
| 51.1 | 36.5 | 7.5 | | 3.2 | | | 1.5 | | | | 0.2 | 1220–1145 | 270 | 255 | 270 |
| 51.1 | 37.0 | 7.0 | | 3.2 | | | 1.5 | | | | 0.2 | 1235–1145 | 270 | 255 | 270 |
| 51.1 | 37.0 | 7.0 | 0.5 | 2.7 | | | 1.5 | | | | 0.2 | 1235–1145 | 260 | 245 | 270 |
| 45.0 | 41.7 | 5.0 | | 4.8 | | | 3.2 | 0.3 | | | | 1210–1140 | 285 | 255 | 360 |
| 45.0 | 41.7 | 4.2 | 0.8 | 4.8 | | | 3.2 | 0.3 | | | | 1210–1140 | 285 | 255 | 340 |
| 40.0 | 46.6 | 5.0 | 0.8 | 4.1 | | | 1.5 | 1.8 | 0.2 | | | 1270–1140 | 201 | 175 | 210 |
| 35.0 | 48.2 | 4.0 | 2.0 | 7.0 | | | 3.5 | 0.3 | | | | 1200–1150 | 321 | 293 | 321 |
| 20.0 | 59.6 | | 6.0 | 10.0 | | | 4.0 | 0.4 | | | | 1210–1150 | 372 | 314 | 412 | g = Cast Hardness
w = Soft Annealed
a = Maximal Hardened

The entire disclosure of German priority application No. P3406712.4 is hereby incorporated by reference.

What is claimed is:

1. A noble metal alloy suitable for dental purposes consisting of 20 to 65% gold, 25 to 65% palladium, 0 to 7% gallium, 0.2 to 11% of at least one of the elements indium and tin, 0 to 2% copper, 0.05 to 1% of at least one of the elements ruthenium, iridium and rhenium, 0 to 1% vanadium, 0 to 1% iron and 0.5 to 15% cobalt, with the proviso that the content of base metals is over 5%.

2. A noble metal alloy according to claim 1 containing 50 to 65% gold, 30 to 40% palladium, 4 to 10% indium, 0 to 2% tin, 1 to 2% gallium, 0.05 to 1% of at least one of the elements ruthenium, rhenium, and iridium, and 1 to 5% cobalt.

3. A noble metal alloy according to claim 2 containing 60 to 65% gold, 30 to 35% palladium, 4.5 to 6% indium, 0 to 2% tin, 1 to 2% gallium, 0.05 to 0.3% of at least one of the elements ruthenium, iridium, rhenium, and 1 to 3% cobalt.

4. A noble metal alloy according to claim 1 containing 50 to 55% gold, 35 to 40% palladium, 6 to 10% indium, 0 to 1% tin, 1 to 2% gallium, 0.05 to 1% of at least one of the elements ruthenium, rhenium, and iridium, 1.5 to 12.5% cobalt, 0 to 1% vanadium, and 0 to 1% iron.

5. A noble metal alloy according to claim 1 containing 20 to 50% gold, 40 to 60% palladium, 0.2 to 8% indium, 0.2 to 6% tin, 0 to 2% copper, 1 to 5% gallium, 0.05 to 1% of at least one of the elements ruthenium, iridium, and rhenium, and 2 to 12% cobalt.

* * * * *